United States Patent [19]

O'Rourke et al.

[11] Patent Number: 6,165,784
[45] Date of Patent: Dec. 26, 2000

[54] ANTIBODIES FOR THE DETECTION OF PRION PROTEIN AS AN INDICATION OF TRANSMISSIBLE SPONGIFORM ENCEPHALOPATHIES

[75] Inventors: Katherine I. O'Rourke, Albion; Donald P. Knowles, Pullman, both of Wash.; Timothy V. Baszler, Moscow, Id.; Steven M. Parish, Pullman, Wash.

[73] Assignees: The United States of America as represented by the Secretary of Agriculture, Washington, D.C.; Washington State University Research Foundation, Pullman, Wash.

[21] Appl. No.: 08/950,271

[22] Filed: Oct. 14, 1997

[51] Int. Cl.$^7$ .............................. C12N 5/06; C12N 5/16; C07K 16/00; C12P 21/08
[52] U.S. Cl. .......................... 435/326; 435/329; 435/331; 530/388.2; 530/388.85
[58] Field of Search .................................. 435/326, 329, 435/331; 530/388.2, 388.85

[56] References Cited

U.S. PATENT DOCUMENTS 4,806,627  2/1989  Wisniewski et al. .

OTHER PUBLICATIONS

Sevier et al (Clinical Chemistry vol. 27 No. 11 pp. 1797–1806), 1981.

K.I. O'Rourke et al., "PrP Genotypes and Experimental Scrapie in Orally inoculated Suffolk Sheep in the United States," *Journal of General Virology* 78:975–978 (1997).

K.I. O'Rourke, T.P. Huff, C.W. Leathers, M.M. Robinson and J.R. Gorham, "SCID0 Mouse Spleen Does Not Support Scrapie Agent Replication," *Journal of General Virology* 75:1511–1514 (1994).

K.I. O'Rourke, R.P. Melco and J.R. Mickelson, "Allelic Frequencies of an Ovine Scrapie Susceptibility Gene," *Animal Biotechnology* 75(2):155–162 (1996).

S.C. Arya, "Diagnosis of New Variant Creutzfeldt–Jakob Disease by Tonsil Biopsy," *The Lancet* 349:1322–1323 (May 1997).

P.E. Bendheim et al., "Nearly Ubiquitous Tissue Distribution of The Scrapie Agent Precursor Protein," *Neurology* 42:149–156 (1992).

W.J. Hadlow, C.M. Eklund, R.C. Kennedy, T.A. Jackson, H.W. Whitford, & C.C. Boyle, "Course of Experimental Scrapie Virus Infection in the Goat," *Journal of Infectious Diseases* 129(5):559–567(1974).

W.J. Hadlow, R.C. Kennedy & R.E Race, "Natural Infection of Suffolk Sheep with Scrapie Virus," *Journal of Infectious Diseases* 146(5):657–664 (1982).

M. Haritani, Y.I. Spencer & G.A.H. Wells, "Hydrated Autoclave Pretreatment Enhancement of Prion Protein Immunoreactivity in Formalin–fixed Bovine Spongiform Encephalopathy–Affected Brain," *Acta Neuropathol* 87:86–90 (1994).

A.F. Hill, M. Zeidler, J. Ironside & J. Collinge, "Diagnosis of New Variant Creutzfeldt–Jakob Disease by Tonsil Biopsy," *The Lancet* 349:99–100 (Jan. 1997).

M. Horiuchi, N. Yamazaki, T. Ikeda, N. Ishiguro & M. Shinagawa, "A Cellular Form of Prion Protein (PrP$^c$) Exists in Many Non–neuronal Tissues of Sheep," *Journal of General Virology* 76:2583–2587 (1995).

Y. Ikegami, M. Ito, H. Isomura, E. Momotani, K. Sasaki, Y. Muramatsu, N. Ishiguro & M. Shinagawa, "Pre–clinical and Clinical Diagnosis of Scrapie by Detection of PrP Protein in Tissues of Sheep," *The Veterinary Record* 128:271–275 (1991).

R.J. Kascsak, R. Fersko, D. Pulgiano, R. Rubinstein & R.I. Carp, "Immunodiagnosis of Prion Disease," *Immunological Investigations* 26(1&2):259–268 (1997).

T. Kawashima, H. Furukawa D. Doh–ura & T. Iwaki, "Diagnosis of New Variant Creutzfeldt–Jakob Disease by Tonsil Biopsy," *The Lancet* 50:68–69 (1997).

P.A. McBride, P. Eikelenboom, G. Kraal, H. Fraser & M.E. Bruce, "PrP Protein is Associated with Follicular Dendritic Cells of Spleens and Lymph Nodes in Uninfected and Scrapie–Infected Mice," *Journal of Pathology* 168:413–418 (1992).

J.M. Miller, A.L. Jenny, W.D. Taylor, R.F. Marsh, R. Rubenstein & R.E. Race "Immunohistochemical Detection of Prion Protein in Sheep with Scrapie," *J Vet Diagn Invest* 5:309–316 (1993).

J.M. Miller et al., "Detection of Prion Protein in Formalin–Fixed Brain by Hydrated Autoclaving Imnmunohistochemistry for the Diagnosis of Scrapie in Sheep," *J Vet Diagn Invest* 6:366–368 (1994).

Y. Muramatsu, A. Onodera, M. Horiuchi, N. Ishiguro & M. Shinagawa, "Detection of PrP$^{Sc}$ in Sheep at the Preclinical Stage of Scrapie and its Significance for Diagnosis of Insidious Infection," *Archives of Virology* 134:427–432 (1993).

Y. Muramatsu, A. Onodera, M. Horiuchi, N. Ishiguro & M. Shinagawa, "The Significance of PrP$^{Sc}$ Detection for the Diagnosis of Insidious Scrapie," *Annals of the New York Academy of Sciences* 724:347–349 (1994).

I.H. Pattison & G.C. Millson, "Distribution of the Scrapie Agent in the Tissues of Experimentally Inoculated Goats," *J Comp Path* 72:233–244 (1962).

(List continued on next page.)

*Primary Examiner*—Albert Navarro
*Attorney, Agent, or Firm*—M. Howard Silverstein; John D. Fado; Margaret A. Connor

[57] ABSTRACT

Methods to detect prion or PrP-Sc protein as an indication of transmissible spongiform encephalopathies (TSEs), including preclinical detection of infected live animals, and postmortem detection methods, are described. In one aspect, the invention is directed to a non-invasive diagnostic assay using third eyelid-associated lymphoid tissue. In another aspect, the invention is directed to monoclonal antibodies that specifically bind a conserved epitope of PrP-Sc protein in fixed or frozen treated tissue.

3 Claims, No Drawings

OTHER PUBLICATIONS

R. Race, D. Ernst, A. Jenny, W. Taylor, D. Sutton & B. Caughey, "Diagnostic Implications of Detection of Proteinase K–Resistant Protein in Spleen, Lymph Nodes, and Brain of Sheep," *Am J Vet Res* 53,6:883–889 (1992).

B.E.C. Schreuder. L.J.M. van Keulen, M.E.W. Vromans, J.P.M. Langeveld & M.A. Smits "Preclinical Test for Prion Diseases," *Nature* 381:563 (1996).

L.J.M. van Keulen, B.E.C. Schreuder, R.H. Meloen, G. Mooij–Harkes, M.E.W. Vromans & J.P.M. Langeveld, "Immunohistochemical Detection of Prion Protein in Lymphoid Tissues of Sheep with Natural Scrapie,"; *Journal of Clinical Microbiology* 35(5):1228–1231 (1996).

L.J.M. van Keulen, B.E.C. Schreuder, R.H. Meloen, M. Poelen–Van Den Berg, G. Mooij–Harkes, M.E.W. Vromans & J.P.M. Langeveld, "Immunohistochemical Detection and Localization of Prion Protein in Brain Tissue of Sheep with Natural Scrapie," *Vet Pathol* 32:299–308 (1995).

6,165,784

ANTIBODIES FOR THE DETECTION OF PRION PROTEIN AS AN INDICATION OF TRANSMISSIBLE SPONGIFORM ENCEPHALOPATHIES

BACKGROUND OF THE INVENTION

1. Field of the Invention

The present invention relates to methods for detection of prion protein (also denoted as PrP-Sc protein) as an indicator of transmissible spongiform encephalopathies. In particular, this invention relates to non-invasive, preclinical methods for detection of prion proteins in ruminants using third eyelid lymphoid tissue. The invention further relates to monoclonal antibodies that specifically bind a conserved epitope of prion proteins in ruminants and immunoassays using the antibodies to detect prion protein in fixed, treated tissue.

2. Description of the Art

Transmissible spongiform encephalopathies (TSEs) are a heterogeneous group of fatal neurodegenerative disorders that occur in humans, ruminant herbivores, mink, and cats. Sheep scrapie is the prototype of this group. TSEs are characterized by deposition of prion proteins (also denoted as PrP-Scrapie or PrP-Sc), the infectious form of the proteins, in the central nervous system of affected individuals. Prions have been defined as small proteinaceous infectious particles which resist inactivation by procedures that modify nucleic acids. The term "prion" is a contraction of the words "protein" and "infection," and prions are comprised largely if not exclusively of PrP-Sc molecules encoded by a PrP gene. Prion diseases are often called spongiform encephalopathies because of the post mortem microscopic or histopathologic appearance of the brain of an infected animal with large vacuoles in the cortex and cerebellum. Prion proteins are insoluble, protease-resistant glycoproteins resulting from post translational modification of normal mammalian glycoproteins (PrP-Cellular or PrP-C), and deposition of the prion protein, an abnormal isoform of a native cellular sialoglycoprotein, in the central nervous system is a reliable marker of TSE infection.

The most widely studied TSEs in food-producing animals include scrapie in sheep and goats, bovine spongiform encephalopathy (BSE) in cattle (also known as "Mad Cow" disease), and chronic wasting disease (CWD) in mule deer and elk. Other TSEs in animals included transmissible mink encephalopathy (TME) in mink and feline spongiform encephalopathy (FSE) of cats. Prion diseases of humans have also been identified. These include: Creutzfeldt-Jakob Disease (CJD); Gerstmann-Straussler-Scheinker Syndrome (GSS); Fatal Familial Insomnia (FFI), and Kuru.

The transmissible agent in these diseases remains controversial. However, as noted above, an insoluble isoform, (prion or PrP-Sc) of a mammalian sialoglycoprotein (PrP-Cellular or PrP-C) is a major component in infectious material. It appears that the scrapie isoform of the prion protein (PrP-Sc) is necessary for both the transmission and pathogenesis of the transmissible neurodegenerative diseases of animals and humans (see S. B. Prusiner, *Science* 252:1515–1522 (1991)). A leading hypothesis is that prion diseases result from the conversion of PrP-C to Prp-Sc by a nucleation or polymerization event.

The occurrence of novel transmissible spongiform encephalopathies in cattle in the United Kingdom and Europe and in mule deer and elk in parts of the United States has emphasized the need for reliable diagnostic tests. Further, the epizootic of a TSE in cattle and its postulated relationship to a new variant of human Creutzfeldt Jakob Disease have increased public and scientific awareness of these relatively rare disorders, and have highlighted the need for preclinical detection of TSEs. Although no cases of BSE have been detected in the United States, sensitive immunohistochemical techniques and preclinical detection methods are basic for detection, surveillance, and control of TSEs.

Prion diseases can have a long incubation period. For example, in sheep it can take 3 to 5 years from the time when an animal becomes infected until it first shows disease signs. In bovine spongiform encephalopathy (BSE) it can take two to eight years from the time when an animal becomes infected until it first shows disease signs. Infected animals and humans have neither a disease-specific immune response nor consistent biochemical, hematological and gross pathological abnormalities. The early diagnosis of transmissible spongiform encephalopathies can therefore be dependent on the appearance of clinical signs, electroencephalography, or the invasive method of taking brain biopsies. Confirmation of TSEs is accomplished by postmortem microscopic or histological examination of brain tissue of suspected cases. Postmortem histopathologic diagnosis of the ruminant TSEs is based on the appearance of neuronal vacuolation, spongiform changes, gliosis, and astrocytosis. However, these can vary in intensity and anatomic location depending on the host species, the individuals, host genetics, stage of disease, and infectious source. Thus, diagnosis by histopathology alone may be equivocal in early cases and usually not possible in autolyzed tissue.

Deposition of prion protein (PrP-Sc) in the central nervous system is a reliable marker for the TSEs. Immunohistochemical detection of PrP-Sc is therefore an important adjunct to histopathology in diagnosis, surveillance, and control of TSEs. Monoclonal antibody 263K 3F4 (U.S. Pat. No. 4,806,627) detects PrP-Sc in hamsters and humans, and has received widespread use in diagnostic assays and pathogenesis studies of human TSEs. A major disadvantage is that it fails to react with PrP from sheep and cattle (R. J. Kascsak et al., *Immunological Investigations* 26:259–268 (1997)). Rabbit antisera reactive with ruminant Prp-Sc has the disadvantages that it cannot be standardized for widespread use due to limitations in quantity and specificity. M. Horiuchi et al. (*Journal of General Virology* 76:2583–2587 (1995)) describe a panel of synthetic peptides that generated monoclonal and polyclonal antibodies reactive with the PrP-Cellular, the non-disease-related protein) in immunoblots of selected sheep and cattle tissue. They did not report effectiveness for detecting the disease-related isoform, PrP-Sc. Additionally, they did not they report effectiveness in detecting either PrP-C or PrP-Sc in formalin fixed tissues.

Post mortem diagnosis of prion diseases is made using histologic and immunohistochemical assays on brain tissue. Ante-mortem testing in humans with suspected CJD is performed by immunohistochemical and histologic examination of brain biopsies. Because brain biopsy in ruminant animals is not feasible, an alternative approach, based on W. J. Hadlow et al's observation (*The Journal of Infectious Diseases* 146:657–664 (1982)), has been to biopsy selected lymph nodes. Hadlow et al. demonstrated that infectivity was detectable in certain lymph nodes (retropharyngeal, tonsil, mesenteric, prescapular, bronchial-mediastinal, and spleen) and the lymphoid tissue in the intestine of scrapie-infected sheep. Hadlow's studies, carried out before the discovery of the prion protein, detected infectivity by mouse inoculation. Race et al. (*American Journal of Veterinary Research* 53:883–889 (1992)), Ikegami et al. (*Veterinary*

Record 128:271–275 (1991)), and van Keulen et al. (*Journal of Clinical Microbiology* 34:1228–1231 (1996)) performed similar surveys by Western immunoblots or immunohistochemical assay of selected lymph nodes using polyclonal antisera. Major disadvantages of these procedures include the following: sampling of these internal tissues requires expensive invasive methods including general anesthesia with its concomitant risks and recovery period; lymphoid tissues of sheep are often infected with a bacteria, *Corynebacterium pseudotuberculosis*, which destroys the architecture of the node and limits its use in these assays; and tonsillar tissue traps environmental antigens, including fungal antigens, some of the which cross react with PrP-Sc, giving equivocal or false positive immunohistochemical reactions which must be resolved by technically demanding Western blot analysis.

The BSE epidemic in the United Kingdom and the European community has cost producers and consumers in direct livestock losses and indirect loss of markets for beef and beef by-products, including economically important pharmaceutical products. Sheep and beef producing countries around the world are conducting costly surveillance and quarantine programs to maintain their status as BSE-free. Most importantly, data from several scientific lines of inquiry have provided strong evidence that BSE has infected humans in Great Britain. The scope of this new disease has yet to be determined.

What are needed is a practical, inexpensive, non-invasive method for detection of PrP-Sc in live animals and sensitive immunohistochemical assays to detect PrP-Sc in animal tissues and animal by-products.

SUMMARY OF THE INVENTION

The present invention relates to methods for detection of prion or PrP-Sc proteins as an indication of transmissible spongiform encephalopathies. In one embodiment, the invention comprises a non-invasive diagnostic assay using third eyelid lymphoid tissue to detect PrP-Sc in ruminants. This method is the first report of the use of third eyelid lymphoid tissue to detect any infectious organism. Further, this is the first report of PrP-Sc in the third eyelid lymphoid tissue.

The third eyelid represents an easily obtainable specimen for testing tissue from live animals or from animals sampled at slaughter. Thus, this detection method provides a much needed practical method for early detection of PrP-Sc and provides a means for preclinical diagnosis of TSEs.

In a second embodiment, the invention comprises monoclonal antibodies that specifically bind a conserved epitope on the ruminant prion proteins. The monoclonal antibodies of the invention react with prion protein in tissues from sheep, cattle, mule deer, and elk with naturally occurring TSE. Additionally, the antibodies detect PrP-Sc in fixed, treated tissue as an indication of the presence of TSE infection, and provide a sensitive reagent for diagnosis of TSEs.

The invention further includes immunoassay methods using the antibodies, including immunohistochemistry assays, Western immunoblots, and dot blots.

In accordance with this discovery, it is an object of the invention to provide methods for detection of prion or PrP-Sc as a marker for TSEs, including preclinical detection of infected live animals, and postmortem detection methods.

Another object of the invention is the provision of a non-invasive diagnostic assay based on biopsy of third eyelid lymphoid tissue and detection of PrP-Sc in situ as a practical method for early detection of PrP-Sc.

A further object of the invention is to provide monoclonal antibodies which recognize a conserved epitope in formalin fixed paraffin sections after treatment, including hydrated autoclaving. These monoclonal antibody reagents to conserved epitopes on PrP-Sc provide specific, reliable, and flexible tools for the accurate diagnosis of TSE. Uses of the antibodies include as reagents for standardized diagnostic testing and comparative pathology studies.

A still further object comprises immunoassay methods useful in diagnostic and pathogenesis studies of TSE in ruminants, and useful for detection, surveillance, and control of TSEs.

Other objects and advantages of the invention will become readily apparent from the ensuing description.

DETAILED DESCRIPTION OF THE INVENTION

In one embodiment, the invention comprises a non-invasive diagnostic assay using third eyelid lymphoid tissue to detect PrP-Sc in ruminants. The nictitating membrane or third eyelid (*palpebra tertia*) of ruminant animals consists of a cartilaginous sheet with superficial lymphoid follicles and a seromucinous secretory gland beneath the conjunctiva of the bulbar surface. Ruminant animals including sheep, goats, mule deer, elk, and cattle have third eyelids.

In the practice of the invention, a sample of nictitating membrane-associated lymphoid tissue is collected from the animal to be tested. This can be readily carried out by everting the third eyelid. Typically two clusters of lymphoid tissue are visualized superior to the more pale glandular tissue. Biopsy of the lymphoid nodule can be performed using only local anesthetic.

The collected tissue sample is then subjected to immunohistochemical or other protein-detecting methods which are capable of detecting prion or PrP-Sc, if present in the tissue. For purposes of this invention, the term prion or PrP-Sc is defined as the disease-related protein that is a marker of TSEs.

Detection methods include immunoassays using polyclonal or monoclonal antibodies that specifically bind an epitope of PrP-Sc, for example, immunohistochemistry assays, Western immunoblots, and dot blots.

A preferred detection method comprises immunoassays using a monoclonal antibody that specifically binds a conserved epitope on the ruminant prion proteins. This antibody is described in detail below in the second embodiment of this invention.

Also preferred is the sensitive immunohistochemical technique described in detail, below, in Example 1. In brief, a fixed tissue section is treated to unmask the epitope to PrP-Sc and enhance antibody binding, and to eliminate availability of the corresponding epitope of PrP-Cellular which is expressed in tissues from normal animals. This can be conveniently carried out by (a) hydrated autoclaving, e.g., by autoclaving hydrated sections in water or buffer at about 121° C. for 20 to 30 minutes, followed by cooling; (b) treatment with 98% formic acid for 30 minutes with or without a subsequent step of hydrated autoclaving, or (c) digestion with trypsin (e.g., 0.1% trypsin for 20 minutes at 37° C. in Tris HCl buffer, pH 7.6). The sample is then incubated with antibody that specifically binds PrP-Sc for a time and under conditions effective to bind PrP-Sc, if present in the tissue.

Bound antibody is detected using known methods. In the preferred embodiment, detection is carried out by two cycles of incubation with a second antibody, e.g., biotinylated anti-mouse IgG, and labeled biotin, e.g., avidin-biotin-horseradish peroxidase complex, with intervening washes in buffer, e.g., Tris-HCl. An indicator such as a chromogen is added to detect bound antibody.

As shown in Example 1, below, using nictitating membrane-associated lymphoid tissue, PrP-Sc was detected in clinically ill (scrapie-infected) and in clinically normal high risk sheep aged 1, 2, and 3 years.

In a second embodiment, the invention comprises monoclonal antibodies that specifically bind a conserved epitope on the ruminant PrP proteins in fixed or frozen tissue that has been treated to unmask the epitope to PrP-Sc and eliminate availability of the corresponding epitope of PrP-C. The monoclonal antibodies of the invention react with PrP-Sc protein in tissues from sheep, cattle, mule deer, and elk with naturally occurring TSE. Presence of PrP-Sc indicates the scrapie-, bovine encephalopathy- or chronic wasting disease-infected animals.

Monoclonal antibodies encompassed by this invention bind the conserved epitope of the PrP gene product in ruminants identified as Ile-His-Phe-Gly. This epitope is further identified as comprising amino acids 142–145 of the ovine (sheep) PrP gene product, which are identical to amino acids 142–145 of the cervid (mule deer and Rocky Mountain elk) PrP gene product and amino acids 150–153 of the bovine PrP gene product. A critical feature of the antibodies of the invention is that they have the further property that they detect the unmasked epitope to PrP-Sc protein in fixed or frozen tissue. Thus, the monoclonal antibodies of the invention provide a sensitive reagent for diagnosis of TSEs.

Exemplary of the monoclonal antibodies of the invention that binds the conserved epitope Ile-His-Phe-Gly of PrP-Sc in fixed or frozen, treated ruminant tissue is monoclonal antibody F89/160.1.5. The isotype of this antibody is IgG1. The immunohistochemical staining pattern of monoclonal antibody F89/160.1.5 was similar to patterns described in the brain of scrapie-affected sheep using polyclonal rabbit antisera to ovine or hamster PrP.

Antibodies of the invention were obtained as described in Example 2, below. In brief, we synthesized a peptide representing bovine residues 146–159, and coupled it to maleimide-activated KLH for use as an immunogen. Antisera and monoclonal antibodies from inoculated mice were screened for reactivity to recombinant sheep PrP to select cross-reacting antibodies. These antibodies were then shown to be reactive with PrP-Sc in formalin fixed, hydrated autoclaved tissue of sheep, cattle, mule deer and elk.

For purposes of this invention, monoclonal antibodies that specifically bind the conserved epitope of PrP-Sc encompassed by this invention are those which are specific for the conserved epitopes of the ruminant PrP-Sc protein, comprising Ile-His-Phe-Gly, as described above, and detect PrP-Sc in fixed or frozen, treated tissue.

The continuous cell line (hybridoma) which produces and secretes monoclonal antibody F89/160.1.5 was deposited on Sep. 24, 1997, with the American Type Culture Collection (ATCC), 10801 University Boulevard, Manassas, Va. 20110-2209 USA, under terms of the Budapest Treaty, and has been assigned accession number ATCC HB-12403.

Another exemplary monoclonal antibody prepared as described in Example 2, below, and which specifically binds the epitope to which monoclonal antibody F89/160.1.5 is directed is monoclonal antibody F89/193.1.5. The continuous cell line (hybridoma) which produces and secretes monoclonal antibody F89/193.1.5 was deposited May 25, 1999, with the American Type Culture Collection (ATCC), 1801 University Blvd., Manassas, Va. 20110-2209 USA, under terms of the Budapest Treaty, and has been assigned accession number ATCC PTA-114.

The antibodies detect PrP-Sc in fixed or frozen, treated tissue as an indication of the presence of TSE infection, and provide a sensitive reagent for diagnosis of TSEs. Tissue samples useful for testing for PrP-Sc include third eyelid-associated lymphoid tissue, brain necropsy tissue, lymph node biopsy or necropsy tissue or spleen biopsy or necropsy tissue. The monoclonal antibody forms an antigen-antibody complex and the bound antibody is detected by immunological means such as enzyme-linked immunoabsorbent assay, Western blot assay, dot blot assay, immunodecoration and immunocytochemistry.

Immunoassay methods using the antibodies are also encompassed by the invention. In brief, to detect PrP-Sc, a tissue sample is obtained from an animal to be tested; the tissue is fixed, for example, by preserving in formalin or paraformaldehyde as known in the art. Next, the fixed tissue section is treated to unmask the epitope to PrP-Sc and eliminate availability of the corresponding epitope of PrP-Cellular which is expressed in tissues from normal animals, as discussed in detail above. The fixed, treated tissue is contacted with the monoclonal antibody of the invention in an amount and under conditions effective to bind PrP-Sc protein if present in the tissue. As noted in the examples, incubation of a tissue sample with about 3 $\mu$g/ml of the monoclonal antibody in buffer overnight at room temperature causes antibody to be bound to the conserved PrP-Sc epitope. The antibody is detected by procedures known in the art as discussed above. In one aspect, the monoclonal antibody bound to the tissue sections is detected by contacting it with a detectably labeled second antibody under conditions such that the second antibody binds to the monoclonal antibody and detecting the second antibody so bound. In a still further aspect, the monoclonal antibody bound to the tissue sections is detected by contacting it with a labeled second antibody under conditions such that the second antibody binds to the monoclonal antibody; then the second antibody is contacted with an enzyme-ligand complex such that the complex binds to the label on the second antibody, and the enzyme-ligand complex is detected, for example, with a chromogenic substrate.

Alternatively, frozen tissue is homogenized in detergent and treated with proteinase K to eliminate the 35 K PrP-C band and reveal the characteristic multiple 28–32 K bands of proteinase K-resistant PrP-Sc fragments. Treated proteins are separated on polyacrylamide gels and transferred to filters. The filter is contacted with the monoclonal antibody of the invention in an amount and under conditions effective to bind PrP-Sc protein if present in the tissue. The antibody is detected as described above except that the preferred final detection step is with a chemiluminescent substrate.

As discussed above, antibodies of the invention are useful in diagnostic and pathogenesis studies of the TSEs.

EXAMPLES

The following examples are intended only to further illustrate the invention and are not intended to limit the scope of the invention which is defined by the claims.

Example 1

The following example describes a noninvasive diagnostic assay using third eyelid lymphoid tissue. A sensitive immunohistochemical technique is also described in this example.

Materials and Methods

Animals Tested. Sheep of the Suffolk, Southdown or Hampshire breeds with clinical signs of scrapie were sampled by biopsy of third eyelid-associated lymphoid tissue before euthanasia or at necropsy. Additional clinically healthy sheep were acquired from flocks with a history of clinical scrapie, confirmed by histology and/or immunohistochemistry of midbrain by the USDA National Veterinary Services Laboratory, Ames, Iowa, USA. Although susceptibility to scrapie has been defined genetically, a large percentage of U.S. Suffolk sheep carrying the susceptible genotype (136 AA, 171 QQ) do not develop scrapie, even in heavily infected flocks. Thus, in the U.S. maternal exposure is a better parameter than PrP genotype when selecting high risk sheep. We defined high risk sheep as first or second generation offspring of scrapie-affected ewes. Ages of high risk sheep in this study ranged from 1 to 5 years at the time of sampling.

Tissue Collection and Preparation. Third eyelid-associated lymphoid tissue was sampled under local anesthesia as follows: a topical anesthetic (Proparacaine HCl (Ophthetic, Allergan, Inc.)) was applied to the medial canthus of the eye, and the third eyelid was everted with disposable 1×2-toothed, 5½ inch forceps (Sklar 78055-1). Typically two clusters of lymphoid tissue were visualized superior to the more pale glandular tissue. One cluster of lymphoid tissue was collected using disposable Metzenbaum scissors (Sklar 30455) and a second set of forceps.

Immunohistochemistry Assay. Tissue sections of one cluster which typically contains 5–15 lymphoid follicles per section were prepared from the cluster that had been fixed in formalin for 24 hours under conventional conditions and embedded in paraffin. Tissue sections were deparaffinized and rehydrated through graded alcohols, then treated by hydrated autoclaving by autoclaving at 121° C. for 20 minutes in 0.01 M Tris-HCl, pH 7.6, to unmask the PrP-Sc epitope and eliminate availability of the corresponding epitope on PrP-Cellular.

The fixed, treated samples were contacted with monoclonal antibody F89/160.1.5 under conditions effective to bind antibody as follows: the samples were incubated overnight at room temperature with monoclonal antibody F89/160.1.5 (3 µg/ml in 0.01 M Tris-HCl buffer, pH 7.6). The negative control was performed by replacing F89/160.1.5 with an IgG1 monoclonal antibody to an irrelevant protein under the same conditions.

Antibody that bound PrP-Sc was detected by two cycles of incubation (40 minutes each) with biotinylated anti-mouse IgG and avidin-biotin-horseradish peroxidase complex with intervening washes in 0.01 M Tris-HCl, pH 7.6, with 0.05% Triton X100. The peroxidase substrate/chromogen (AEC, DAKO Corp.) was applied twice with no intervening washes. Slides were counterstained with Mayer's hematoxylin and mounted in GelTol medium (Lipshaw Immunon, Pittsburg, Pa.).

Results

Immunohistochemistry assay of nictitating membrane-associated lymphoid follicles was positive in 19 sheep from 7 flocks of origin. All had the susceptible PrP genotype 136 AA, 171 QQ.

The nictitating membrane-associated lymphoid tissue from high risk scrapie sheep showed distinct, punctate multifocal PrP-Sc deposition (immunostaining red) within lymphoid follicle germinal centers. Most immunoreactivity within germinal centers was located in the cytoplasm of multipolar cells which were sometimes rimmed by mature lymphocytes, characteristics of follicular dendritic cells. Immunoreactivity was also associated with phagocytized debris in cells with the nuclear morphology of resident macrophages.

No staining was observed in lymphoid follicles of high risk sheep when monoclonal antibody F89/1160.1.5 was replaced by an isotype control or when nictitating membranes from 10 sheep with no known exposure to scrapie were examined with monoclonal antibody F89/160.1.5.

At least 5 lymphoid follicles were examined in all cases. The intensity and pattern of PrP-Sc immunoreactivity in formalin-fixed lymphoid tissues treated with hydrated autoclaving was similar to that of paired samples fixed in paraformaldehyde and treated with formic acid and hydrated autoclaving.

This test provides a practical method for early detection of scrapie infected sheep.

Example 2

The following example describes preparation and characterization of monoclonal antibodies which specifically bind the conserved epitope of PrP-Sc in ruminants.

In brief, five mice were immunized with a KLH-conjugated synthetic peptide representing residues 146–159 of the bovine prion gene product. Antisera and hybridoma supernatants were screened by ELISA using a recombinant sheep PrP fusion protein as antigen. Cell line F89/160 produced antibodies reactive in ELISA and was selected for two rounds of cloning by limiting dilution. Hybridoma cells from this cloned line were transferred to an in vitro artificial capillary cell culture production system. Monoclonal antibody F89/160.1.5 (IgG1) with a concentration of 3.64 mg/ml was further characterized by epitope mapping, immunoblot analysis, and immunohistochemistry.

Materials and Methods

Antigen preparation and Monoclonal Antibody Production. The peptide $NH_2$-Ser-Arg-Pro-Leu-Ile-His-Phe-Gly-Ser-Asp-Tyr-Glu-Asp-Arg-COOH, representing residues 146–159 of the bovine prion gene (Horiuchi et al., supra), was synthesized and coupled to maleimide-activated keyhole limpet hemocyanin (KLH) (Pierce Chemical Company). Five 6-week old BALB/c mice were each inoculated subcutaneously in two sites with a total of 10 µg conjugated peptide emulsified in 200 µl Freund's complete adjuvant. Two booster inoculations of 10 µg conjugated peptide in 200 µl Freund's incomplete adjuvant were administered at 14 day intervals. Sera collected by tail vein venipuncture were assayed by ELISA using a recombinant ovine PrP-C as antigen (see below). Three days before cell fusion, mice were immunized intravenously with 10 µg conjugated peptide in phosphate buffered saline (PBS) without adjuvant. Cell fusion and cloning by limiting dilution were performed following standard protocols (W. M. Yokoyama, In: J. E. Coligan (ed.), *Current Protocols in Immunology*, Wiley Intersciences, New York, p. 2.2.1–2.5.17 (1994)). Supernatants from primary and cloned hybridomas were screened by recombinant ovine PrP-C ELISA. Clone 1.5 from cell line F89/160 was selected and transferred to an artificial capillary cell culture system (CellMax, CellCo Inc.) for in vitro production of monoclonal antibody supernatant. Supernatants were collected daily and pooled. Heavy chain isotype was identified by ELISA and monoclonal antibody concentration by immunodiffusion.

Production of Recombinant Sheep PrP-C in *Escherichia Coli*. Genomic DNA was isolated from peripheral blood mononuclear cells of a Suffolk sheep. The PrP open reading frame was amplified with flanking primers (D. Westaway et al., *Genes Devel.* 8:959–969 (1994)) modified to incorporate EcoRI restriction sites:

forward primer: 5'-ATCGAATTCAAGAAGCG ACCAAAAC-3' reverse primer: 5'-ATCGAATTCAGACACCACCACT-3'.

The 786 bp PCR product was digested with EcoRI, purified on agarose gels, and ligated into the vector pMal-cRI. Transformation of *E. coli* strain DH5 was performed following conventional techniques. Transformants were screened by PCR of colony minipreps using the cloning primers. One positive clone (pMal-1) was selected for large scale fusion protein expression. The fusion product ShPrP-MBP was isolated from bacterial lysates by affinity chromatography on amylose resin columns and eluted with 10 mM maltose. Fractions were screened by Western immunoblot using a rabbit antiserum to PrP peptide $NH_2$-Gly-Gln-Gly-Gly-Gly-Thr-His-Asn-Gln-Trp-Asn-Lys-Pro-Ser-Lys-COOH (R2843) (K. I. O'Rourke et al., *J. Gen. Virol.* 75:1511–1514 (1994)).

Enzyme-linked Immunosorbent Assay (ELISA). Immulon 2 plates were coated with 6.25 µg per well recombinant ShPrP-MBP fusion protein in 50 µl 0.05 M carbonate buffer, pH 9.6, overnight at 4° C. The plates were blocked with a 1:15 dilution of commercially available milk-based blocker (KPL, Gaithersburg, Md.) for one hour. 50 µl of antisera or hybridoma supernatant were incubated in each well for 30 minutes at room temperature. Plates were developed with goat anti-mouse-horseradish peroxidase and 2,2'-azino-di[3-ethyl-benzthiazoline sulfonate] (R. Fatzer et al., *Zentralbl. Veterinarmed. A.* 43: 23–29 (1996)) (ABTS) (KPL, Gaithersburg, Md.). Optical density was read at 405 nm. Negative controls included sera from uninoculated mice, supernatants from isotype-matched monoclonal antibodies of irrelevant specificity, or tissue culture medium adjusted to 15% fetal calf serum. Positive control wells were incubated with rabbit anti-PrP peptide antiserum (R2843) and developed with goat anti-rabbit-HRPO and ABTS. Positive wells had $OD_{405}$ higher than two standard deviations above the mean of 4 negative control wells.

Defining the Epitope Bound by Monoclonal Antibody F89/160.1.5. Nested sets of hexamer peptides spanning Ser-Arg-Pro-Leu-Ile-His-Phe-Ser-Gly-Asp-Tyr-Glu-Asp-Arg were synthesized on a membrane support using commercial reagents and instructions (SPOTs Test, Cambridge Research Biochemicals, Cheshire, England). The ability of monoclonal antibody F89/160.1.5 to bind to individual hexamer peptides was determined visually following incubation with β-galactosidase-conjugated secondary antibody and substrate.

Source and PrP Gene Sequence of Ruminant Herbivores with Naturally Occurring TSEs. Brain tissues from 34 sheep with histopathological lesions of scrapie were tested for reactivity with monoclonal antibody F89/160.1.5 by immunohistochemistry. PrP-Sc had been detected immunohistochemically using a rabbit anti-hamster PrP polyclonal antiserum in 20 of these samples and by Western immunoblot in 6 of the 20 (J. M. Miller, *Diagn Invent.* 5:309–316 (1993)). Three sheep with no histological lesions of scrapie and no PrP-Sc detectable in Western blot analysis were used as negative controls. These tissues were provided by pathologists in veterinary medical colleges and state diagnostic laboratories or by personnel from the USDA Animal and Plant Health Inspection Service. Brain samples from 10 mule deer (*Odocoileus hemionus hemionus*) and 4 elk (*Cervus elaphus nelsoni*) with naturally occurring CWD were provided by the Colorado State Diagnostic Laboratory and the Colorado Division of Wildlife. Unstained sections from 19 cattle with BSE and 5 BSE-negative cattle were provided by the Pathobiology Laboratory, National Veterinary Services Laboratories, USDA-APHIS, Ames, Iowa. The source of paraffin blocks for these sections was Dr. Gerald Wells, Ministry of Agriculture, Fisheries and Food, Central Veterinary Laboratory, New Haw, Surrey, United Kingdom.

Frozen brain tissue for PrP genotype analysis was available from 12 of 34 scrapie-positive sheep, all 10 mule deer with CWD, and 2 of 4 CWD-affected elk. Blood samples were also available from 39 healthy mule deer and 19 healthy elk. The open reading frame of the PrP gene of the sheep was amplified by the polymerase chain reaction as described above and the polymorphic region from codons 112–240 was sequenced on both strands by automated fluorescent dye labeled dideoxy strand termination (K. I. O'Rourke et al. *Anim. Biotech.* 7:155– 162 (1996)). 100 to 800 ng of genomic DNA from mule deer or elk was amplified using species-specific primers:

forward 5'CTGCAAGAAGCGACCAAAACC reverse 5'CACAGGAGGGGAGGAGAAGAGGAT under standard conditions except that the $Mg^{+2}$ concentration was increased to 2.5 mM. PCR products were sequenced on both strands using forward primer 5'GGCTATCCACCTCAGGGAG reverse primer 5'TCACACTTGCCCCCTCTITGGT which typically yielded sequence information on codons 106 to 224.

Immunoblot Analysis. PrP-Sc was isolated from the brain of sheep with histopathologic lesions of scrapie by differential centrifugation from a high salt Sarkosyl buffer (M. J. Stack et al., pages 85–103, and B. Caughey et al., pages 285–299, both In: H. F. Baker and R. M. Ridley (eds.), *Prion Diseases*, Humana Press, Totowa, N.J. (1996)). Briefly, 0.3 g aliquots of midbrain or brainstem were homogenized in 3.2 ml 10% sarkosyl in TBS (130 mM NaCl, 50 mM Tris-HCl, 7.4) and clarified by centrifugation at 28,000×g for 30 minutes at 10° C. using a Beckman 100.4 rotor in a Beckman TLX ultracentrifuge. The supernatant was centrifuged at 180,000×g for 2.5 hours at 4° C. The resulting pellet was resuspended in TBS/10%/NaCl/1% sarkosyl for 1 hour at 37° C. and repelleted at 250,000×g for 90 minutes. The pellet was resuspended in 0.5 ml 10 mM Tris-HCl, 5 mM $MgCl_2$, 100 mM NaCl, pH 7.4 and digested with DNaseI (20 µg/ml) and Rnase (100 µg/ml) for one hour at 37° C. The buffer was re-adjusted to 3.2 ml TBS/10% NaCl/1% sarkosyl with 10 µg/ml proteinase K and digestion proceeded for 1 hour at 37° C. The reaction was stopped by the addition of Pefabloc (Boerhinger-Mannheim) to 4 mM. PrP-Sc was pelleted by centrifugation at 250,000×g for 90 minutes. The final pellet was boiled in SDS (5%) sample buffer for 10 minutes. Aliquots equivalent to 125 mg starting material were electrophoresed through a 15% polyacrylamide minigel (BioRad) and transferred to PVDF membranes (Schleicher and Scheull). The filters were developed with 3 µg/ml monoclonal antibody F89/160.1.5 or a control antibody, goat anti-mouse IgG-HRPO, and a chemiluminescent substrate (Amersham). Filters were exposed to film (Amersham HyperFilm) for 20 to 120 minutes.

Immunohistochemistry. Brains were fixed in 10% buffered formalin by immersion and embedded in paraffin. One section from each block was stained with hematoxylin and eosin for routine histopathology. Additional tissue sections were mounted on positively charged glass slides (Probe-On Plus, Fisher Scientific) for immunohistochemistry. Sections for immunohistochemistry were deparaffinized and hydrated to 0.1 M Tris, pH 7.5 with 0.1 M NaCl and 0.25% Tween 20 (TNTw). The hydrated slides were autoclaved in distilled water at 121° C. for 30 minutes and allowed to cool. Slides were immunostained using capillary flow technology in an automated immunostainer (Code-On Slide Stainer, Fisher Scientific) as described in J. M. Miller et al., *J. Vet. Diagn. Invest.* 5:309–316 (1993) and J. M. Miller et al., *J. Vet. Diagn. Invest.* 6:366–368 (1994) with the following modifications. Slides were incubated sequentially in blocker (5% normal goat serum in TNTw) for 20 minutes; monoclonal antibody F89/160.1.5 or an IgG1 monoclonal control antibody diluted to 3 μg/ml in blocker overnight at 4° C.; biotinylated anti-mouse IgG (Vector Laboratories) diluted 1:200 in blocking buffer for 30 minutes at 37° C.; streptavidin-alkaline phosphate complex (Biomeda Corp.) for 20 minutes at 37° C.; and 3 applications (5, 5, and 10 minutes without intervening rinses) in a chromogenic alkine-phosphatase substrate (Vector Red™, Vector Laboratories). Slides were counterstained with Gill no. 2 hematoxylin. Tissues were dehydrated and mounted in a xylene-compatible medium (Permount, Fisher Scientific) for application of coverslips. Negative controls consisted of (1) substitution of monoclonal antibody F89/160.1.5 with a similar concentration of irrelevant monoclonal antibody of the same isotype and (2) incubation of monoclonal antibody F89/160.1.5 with brain tissue from scrapie-free sheep as indicated by histopathology and Western blot analysis.

Mule deer and Elk PrP Gene Sequences. Three alleles of the mule deer PrP sequence were identified. Alleles 138S2 (GenBank accession AF009180) and 138N1 (accession U97331) encode Ser and Asn at codon 138. Allele S1 (accession AF009181) differs from S2 by a silent mutation. Two alleles of the elk PrP gene (GenBank AF016227, AF016228) were found, encoding an M→L substitution at codon 132.

Results

Epitope Mapping and Sequence Determination. The epitope recognized by monoclonal antibody F89/160.1.5 was mapped with a panel of overlapping peptides. Residues 142–145 (Ile-His-Phe-Gly) were found to be sufficient for antibody binding. This sequence is conserved in the deduced amino acid sequences of cattle, sheep, mule deer and elk PrP. Polymorphisms at ovine PrP codons 112, 136, 141, 154, 171, and 211 have been reported. Changes at 136 and 171 control susceptibility; substitutions at the other sites may affect incubation time or lesion patterns. We have sequenced the PrP open reading frame in the tissue of 70 U.S. sheep with naturally occurring scrapie. One sheep carried the genotype 136 AV 171 QQ; the other sheep were homozygous for 136 AA, 171 QQ. Brain samples from sheep of both genotypes stained with monoclonal antibody F89/160.1.5. Three alleles of the mule deer PrP gene encode a single amino acid change (N→S) at cervid codon 138. Tissue from CWD-affected mule deer with genotypes 138 NS and 138 SS stained with monoclonal antibody F89/160.1.5. No CWD affected deer homozygous for 138 NN have been identified yet in our survey. A single polymorphism in the elk PrP gene encodes a M→L substitution at cervid codon 132. Samples from 4 CWD-affected elk were available for immunostaining. Frozen tissue for DNA analysis was available from only 2 of these; both were homozygous for 132M.

Immunoblot Reactivity with PrP-Sc from TSE-affected Sheep. The specificity of monoclonal antibody F89/160.1.5 was evaluated by Western blot analysis of PrP-Sc preparations from sheep with natural scrapie and from normal sheep. Peptide bands with apparent molecular weights between 28–35 K were detected in extracts from brain from scrapie-affected sheep. No bands were detectable in extracts from normal sheep brain or when an isotype-matched control monoclonal antibody was used.

Immunohistochemistry of Tissues from Normal and TSE-affected Ruminants. Monoclonal antibody F89/160.1.5 was further evaluated by immunohistochemistry for reactivity on formalin fixed paraffin embedded brain tissue processed routinely for histopathologic examination. All TSE-affected animals had neuropil spongiosis, intraneuronal vacuoles and gliosis within selected brainstem and midbrain nuclei, lesions diagnostic of TSE. At a minimum, the mesencephalon (at the level of the rostral colliculus) and myelencephalon (at the level of the obex) were selected for examination by immunohistochemistry. Heat treatment by autoclaving in water was necessary to unmask the PrP-Sc epitope binding monoclonal antibody F89/160.1.5.

Positive staining was detected in brain from 34 sheep with natural scrapie, 10 mule deer and 4 elk with CWD, and 19 cattle with BSE. Reactivity was limited to gray matter in the midbrain and brainstem, was concentrated in affected nuclei, and was present in the neuropil, and within neurons and glial cells. Most immunostaining consisted of dense granules or plaques randomly within the gray matter neuropil. Often, PrP-Sc aggregated adjacent to glial cell nuclei and accumulated in a branching pattern around glial cells identified histologically as microglia (small, oval to angular hyperchromatic nuclei without recognizable cytoplasm). There was occasional perivascular and subependymal rimming of PrP-Sc reminiscent of astroglial foot processes. Neuronal reactivity consisted of punctate immunostaining within neuronal soma or distinct rimming of neuronal soma with PrP-Sc, either within neuronal membranes or within perineuronal glial processes. Both neurons with and without intraneuronal vacuoles had PrP-Sc reactivity. No reactivity was detected in brain of unaffected sheep, deer, elk or cattle immunostained with monoclonal antibody F89/160.1.5 or in brain from 34 scrapie-affected sheep or 19 BSE-positive cattle immunostained with isotype control monoclonal antibody.

It is understood that the foregoing detailed description is given merely by way of illustration and that modification and variations may be made within, without departing from the spirit and scope of the invention.

What is claimed is:

1. A hybridoma cell line, ATCC HB-12403, which produces and secretes monoclonal antibody F89/160.1.5, which specifically binds to a conserved epitope in sheep, mule deer and elk, and cattle, designated as Ile-His-Phe-Gly, SEQ ID NO:9, and which is capable of binding prion protein (PrP-Sc protein) in fixed or frozen tissue that has been treated to unmask said epitope to PrP-Sc protein and eliminate availability of a corresponding epitope of PrP-Cellular.

2. A monoclonal antibody which specifically binds to a conserved epitope in sheep, mule deer and elk, and cattle, designated as Ile-His-Phe-Gly, SEQ ID NO:9, and capable of binding PrP-Sc protein in fixed or frozen tissue that has been treated to unmask said epitope to PrP-Sc protein and eliminate availability of a corresponding epitope of PrP-Cellular, wherein said monoclonal antibody is F89/160.1.5 (ATCC HB-12403) or F89/193.1.5 (ATCC PTA-114).

3. A hybridoma cell line, ATCC PTA-114, which produces and secretes monoclonal antibody F89/193.1.5, which specifically binds to a conserved epitope in sheep, mule deer and elk, and cattle, designated as Ile-His-Phe-Gly, SEQ ID NO:9, and which is capable of binding prion protein (PrP-Sc protein) in fixed or frozen tissue that has been treated to unmask said epitope to PrP-Sc protein and eliminate availability of a corresponding epitope of PrP-Cellular.

* * * * *

SEQUENCE LISTING

<160> NUMBER OF SEQ ID NOS: 9

<210> SEQ ID NO 1
<211> LENGTH: 14
<212> TYPE: PRT

```
<213> ORGANISM: Bos taurus
<300> PUBLICATION INFORMATION:
<303> JOURNAL: J. Gen. Virol.
<304> VOLUME: 76
<306> PAGES: 2583-2587
<307> DATE: 1995

<400> SEQUENCE: 1

Ser Arg Pro Leu Ile His Phe Gly Ser Asp Tyr Glu Asp Arg
 1               5                  10

<210> SEQ ID NO 2
<211> LENGTH: 25
<212> TYPE: DNA
<213> ORGANISM: Ovis aries
<300> PUBLICATION INFORMATION:
<303> JOURNAL: Genes Dev.
<304> VOLUME: 8
<306> PAGES: 959-969
<307> DATE: 1994

<400> SEQUENCE: 2
atcgaattca agaagcgacc aaaac                                           25

<210> SEQ ID NO 3
<211> LENGTH: 22
<212> TYPE: DNA
<213> ORGANISM: Ovis aries
<300> PUBLICATION INFORMATION:
<303> JOURNAL: Genes Dev.
<304> VOLUME: 8
<306> PAGES: 959-969
<307> DATE: 1994

<400> SEQUENCE: 3
atcgaattca gacaccacca ct                                              22

<210> SEQ ID NO 4
<211> LENGTH: 15
<212> TYPE: PRT
<213> ORGANISM: Mesocricetus auratus
<300> PUBLICATION INFORMATION:
<303> JOURNAL: J. Gen. Virol.
<304> VOLUME: 67
<306> PAGES: 1745-1750
<307> DATE: 1986

<400> SEQUENCE: 4

Gly Gln Gly Gly Gly Thr His Asn Gln Trp Asn Lys Pro Ser Lys
 1               5                  10                  15

<210> SEQ ID NO 5
<211> LENGTH: 21
<212> TYPE: DNA
<213> ORGANISM: Odocoileus hemionus hemionus

<400> SEQUENCE: 5
ctgcaagaag cgaccaaaac c                                               21

<210> SEQ ID NO 6
<211> LENGTH: 24
<212> TYPE: DNA
<213> ORGANISM: Odocoileus hemionus hemionus

<400> SEQUENCE: 6
cacaggaggg gaggagaaga ggat                                            24
```

```
<210> SEQ ID NO 7
<211> LENGTH: 19
<212> TYPE: DNA
<213> ORGANISM: Odocoileus hemionus hemionus

<400> SEQUENCE: 7
ggctatccac ctcagggag                                               19

<210> SEQ ID NO 8
<211> LENGTH: 22
<212> TYPE: DNA
<213> ORGANISM: Odocoileus hemionus hemionus

<400> SEQUENCE: 8
tcacacttgc cccctctttg gt                                           22

<210> SEQ ID NO 9
<211> LENGTH: 4
<212> TYPE: PRT
<213> ORGANISM: Bos taurus

<400> SEQUENCE: 9

Ile His Phe Gly
```